(12) United States Patent
Shimizu et al.

(10) Patent No.: US 10,646,328 B2
(45) Date of Patent: May 12, 2020

(54) TORIC OPHTHALMIC LENS

(71) Applicant: KOWA COMPANY, LTD., Nagoya-shi, Aichi (JP)

(72) Inventors: Kimiya Shimizu, Musashino (JP); Haruo Ishikawa, Nagoya (JP)

(73) Assignee: KOWA COMPANY, LTD., Nagoya-Shi, Aichi (JP)

( * ) Notice: Subject to any disclaimer, the term of this patent is extended or adjusted under 35 U.S.C. 154(b) by 0 days.

(21) Appl. No.: 15/111,158

(22) PCT Filed: Jan. 16, 2015

(86) PCT No.: PCT/JP2015/051115
§ 371 (c)(1),
(2) Date: Jul. 12, 2016

(87) PCT Pub. No.: WO2015/108156
PCT Pub. Date: Jul. 23, 2015

(65) Prior Publication Data
US 2016/0331522 A1 Nov. 17, 2016

(30) Foreign Application Priority Data

Jan. 16, 2014 (JP) .................. 2014-006171

(51) Int. Cl.
*A61F 2/16* (2006.01)
*G02C 7/04* (2006.01)
*G02C 7/02* (2006.01)

(52) U.S. Cl.
CPC ............. *A61F 2/1645* (2015.04); *G02C 7/02* (2013.01); *G02C 7/022* (2013.01); *G02C 7/04* (2013.01); *G02C 2202/06* (2013.01)

(58) Field of Classification Search
CPC ......... A61F 2/1645; G02C 7/02; G02C 7/022; G02C 7/04; G02C 2202/06; B29D 11/00019
(Continued)

(56) References Cited

U.S. PATENT DOCUMENTS

| 6,142,625 A | 11/2000 | Sawano et al. |
| 9,046,698 B2 | 6/2015 | Hansen et al. |
| (Continued) | | |

FOREIGN PATENT DOCUMENTS

| CN | 102171599 A | 8/2011 |
| CN | 102307514 A | 1/2012 |
| (Continued) | | |

OTHER PUBLICATIONS

International Search Report for International Application No. PCT/JP2015/051115, dated Feb. 17, 2015.
(Continued)

*Primary Examiner* — David H Willse
*Assistant Examiner* — Tiffany P Shipmon
(74) *Attorney, Agent, or Firm* — Knobbe, Martens, Olson & Bear LLP (57) ABSTRACT

A toric ophthalmic lens is described in which refractivity of the lens differs between a first direction on a plane perpendicular to an optical axis of the lens and a second direction which differs from the first direction on the plane. In addition, refractivity difference which is the difference between the refractivity in the first direction and the refractivity in the second direction varies depending on a position of the lens in a radial direction.

9 Claims, 6 Drawing Sheets

(58) Field of Classification Search
USPC .................................. 351/159.21, 159.38
See application file for complete search history.

(56) References Cited

U.S. PATENT DOCUMENTS

| | | | |
|---|---|---|---|
| 2006/0055877 A1 | 3/2006 | Yanari | |
| 2008/0013043 A1 | 1/2008 | Ye et al. | |
| 2009/0323020 A1* | 12/2009 | Zhao | A61F 2/1613 351/159.44 |
| 2010/0079723 A1* | 4/2010 | Kingston | A61F 2/1613 351/159.54 |
| 2010/0208194 A1 | 8/2010 | Gupta et al. | |
| 2010/0208195 A1 | 8/2010 | Gupta et al. | |
| 2010/0274234 A1 | 10/2010 | Liang | |
| 2011/0037942 A1 | 2/2011 | Lieberman et al. | |
| 2011/0102738 A1 | 5/2011 | Gupta et al. | |
| 2011/0228225 A1 | 9/2011 | Liang | |
| 2012/0192991 A1 | 8/2012 | Gupta et al. | |
| 2013/0050638 A1 | 2/2013 | Suzaki et al. | |
| 2013/0050640 A1* | 2/2013 | Fiala | G02C 7/041 351/159.43 |
| 2013/0100410 A1 | 4/2013 | Liang | |
| 2013/0107202 A1 | 5/2013 | Liang | |
| 2013/0324983 A1 | 12/2013 | Liang | |
| 2014/0016089 A1 | 1/2014 | Gupta et al. | |
| 2014/0368795 A1 | 12/2014 | Liang | |
| 2015/0248022 A1 | 9/2015 | Gupta et al. | |
| 2015/0305619 A1 | 10/2015 | Liang | |
| 2016/0242641 A1 | 8/2016 | Liang | |
| 2017/0245758 A1 | 8/2017 | Liang | |

FOREIGN PATENT DOCUMENTS

| | | |
|---|---|---|
| EP | 0949529 A2 | 10/1999 |
| EP | 0949529 A3 | 1/2000 |
| JP | 11-295668 A | 10/1999 |
| JP | 2001-021846 A | 1/2001 |
| JP | 2004-133024 A | 4/2004 |
| JP | 2005-201971 A | 7/2005 |
| JP | 4195663 B2 | 12/2008 |
| JP | 2009-544059 A | 12/2009 |
| JP | 4510177 B2 | 7/2010 |
| JP | 2011-502011 A | 1/2011 |
| JP | 2011-526695 A | 10/2011 |
| JP | 2011-221446 A | 11/2011 |
| JP | 2012-504785 A | 2/2012 |
| JP | 2012-510642 A | 5/2012 |
| JP | 2012-518198 A | 8/2012 |
| JP | 2012-233933 A | 11/2012 |
| JP | 2013-178517 A | 9/2013 |
| WO | WO 2010/065475 A2 | 6/2010 |
| WO | WO 2012/149056 A1 | 11/2012 |
| WO | WO 2013/149303 A1 | 10/2013 |

OTHER PUBLICATIONS

Office Action received in connection with corresponding Chinese Patent Application No. 201580004731.6 dated Jun. 21, 2018.
Extended European Search Report for European Patent Application No. 15737580.9, dated Aug. 11, 2017, in 8 pages.
Notification of Reasons for Refusal received in Japanese Patent Application No. 2015-557895 dated Jan. 22, 2019.
Decision of Refusal issued in corresponding Japanese Patent Application No. 2015-557895 dated Jun. 11, 2019.
Decision on Rejection in Chinese Patent Application No. 201580004731.6 dated Jul. 17, 2019.

* cited by examiner

| INTRAOCULAR LENS | BEST FOCUSING | IMAGE PLANE +0.04mm | IMAGE PLANE -0.04mm |
|---|---|---|---|
| CONVENTIONAL TORIC LENS | | | |
| TORIC LENS IN PRESENT EMBODIMENT | | | |

| INTRAOCULAR LENS | BEST FOCUSING | IMAGE PLANE +0.04mm | IMAGE PLANE -0.04mm |
|---|---|---|---|
| CONVENTIONAL TORIC LENS | | | |
| TORIC LENS IN PRESENT EMBODIMENT | | | |

FIG. 6A EYE INTO WHICH TORIC INTRAOCULAR LENS OF PRESENT INVENTION IS INSERTED

BEST FOCUSING

FIG. 6B EYE INTO WHICH TORIC INTRAOCULAR LENS OF PRESENT INVENTION IS INSERTED (+) DEFOCUSING

FIG. 6C EYE INTO WHICH TORIC INTRAOCULAR LENS OF PRESENT INVENTION IS INSERTED (−) DEFOCUSING

TORIC OPHTHALMIC LENS

CROSS-REFERENCE TO RELATED APPLICATION

This application is the U.S. National Phase under 35 U.S.C. § 371 of International Application PCT/JP2015/051115, filed Jan. 16, 2015, which is based upon and claims the benefit of priority of the prior Japanese Patent Application No. 2014-006171, filed on Jan. 16, 2014, the entire contents of which are incorporated herein by reference.

FIELD

The embodiments discussed herein pertain to a toric ophthalmic lens for correcting astigmatism.

BACKGROUND

As examples of an ophthalmic lens for correcting astigmatism, eyeglasses, contact lenses, intraocular lenses and the like are named. These ophthalmic lenses have an optical surface referred to as a toric surface. It is noted that "toric surface" is a surface shape of a lens where radii of curvature of at least two meridians differ from each other as in the case of a side surface of a rugby ball or a doughnut. Accordingly, a lens having such a toric surface is referred to as a toric lens (circular annular lens).

Due to a toric surface, the refractivity of a lens differs between directions orthogonal to each other which are set on the toric surface. Astigmatism can be corrected by making use of the difference in refractivity. In general, this difference in refractivity is referred to as cylindrical refractivity. On a toric surface, a meridian in a direction where refractivity is large is referred to as a steep meridian, and a meridian in a direction where refractivity is small is referred to as a flat meridian. Further, an average value of refractivities on these two meridians is referred to as spherical equivalent power (or simply referred to as spherical power). Usually, in an ophthalmic lens for correcting astigmatism, as indexes indicative of optical performances, equivalent spherical power and cylindrical refractivity are used. Conventionally, there has been proposed a lens where, with respect to optical surfaces disposed in front of and behind the lens, a function of correcting astigmatic abnormality in vision is imparted to one optical surface, and a function of correcting spherical aberration is imparted to the other optical surface (patent literature 1).

CITATION LIST

Patent Literature

[PTL 1] JP-A-2009-544059

SUMMARY

Technical Problem

Recently, along with the development of measuring instruments in ophthalmology, cornea astigmatism in an eyeball can be accurately measured. For example, in an anterior eye part shape analyzer such as Pentacam (registered trademark) (made by OCULUS) or TMS-5 (made by TOMEY CORPORATION), a shape of cornea can be measured, and the distribution of refractive power from the center to the periphery of the cornea can be measured. The substantially same measurement can be also applied to an eye having astigmatism so that amounts of astigmatism ranging from the center to the periphery of a cornea can be also measured.

However, in the conventional ophthalmic lens for correcting astigmatism, only the configuration where one optical surface of the lens is used as a toric surface is disclosed, and a control of cylindrical refractivity on the toric surface is not taken into consideration. Accordingly, even when amounts of astigmatism ranging from the center to the periphery of a cornea can be grasped by the above-mentioned measurement, astigmatism components cannot be properly removed over the whole cornea in the conventional ophthalmic lens for correcting astigmatism whereby the proper improvement of visual functions is limited.

The technique of this disclosure is made in view of the above-mentioned circumstances, and it is an object of this disclosure to realize a toric ophthalmic lens capable of more properly correcting amounts of astigmatism of a cornea.

Solution to Problem

According to an embodiment, it is provided A toric ophthalmic lens wherein refractivity of the lens differs between a first direction on a plane perpendicular to an optical axis of the lens and a second direction which differs from the first direction on the plane, wherein refractivity difference which is the difference between the refractivity in the first direction and the refractivity in the second direction varies depending on a position of the lens in a radial direction. Further, according to the toric ophthalmic lens of the present embodiment, the refractivity difference varies so as to attenuate a variation in refractivity with respect to a radial direction or a circumferential direction in a cornea of an eyeball in which the lens is mounted. With such a configuration, by controlling a amounts of astigmatism in the center portion of the lens and a amounts of astigmatism in the peripheral portion of the lens respectively, it is possible to provide a toric ophthalmic lens which can more properly perform correction of astigmatism compared to a prior art.

In addition, the toric ophthalmic lens according to the present disclosure is the toric ophthalmic lens wherein with respect to first refractivity in a paraxial portion of the lens in the first direction, second refractivity in a peripheral portion of the lens in the first direction, third refractivity in the paraxial portion of the lens in the second direction, and fourth refractivity in the peripheral portion of the lens in the second direction, the difference between the first refractivity and the third refractivity is refractivity difference in the paraxial portion of the lens and the difference between the second refractivity and the fourth refractivity is refractivity difference in the peripheral portion of the lens, and the refractivity difference in the paraxial portion of the lens and the refractivity difference in the peripheral portion of the lens are controlled to be different from each other. Alternatively, there is provided the toric ophthalmic lens, wherein amounts of first spherical aberration in the first direction and amounts of second spherical aberration in the second direction are controlled individually.

Advantageous Effects of Invention

According to the technique of this disclosure, it is possible to realize a toric ophthalmic lens capable of more properly correcting amounts of astigmatism of an eyeball.

DESCRIPTION OF EMBODIMENTS

Hereinafter, an embodiment of the present invention is described with reference to drawings. Although a toric intraocular lens will be described in the description made hereinafter, the present invention is not limited to the intraocular lens and is also applicable to various ophthalmic lenses including contact lenses.

Firstly, spherical aberration which is one of Seidel's five aberrations is described with reference to FIG. 1. When spherical aberration occurs, power difference is generated between a center portion (paraxial portion) and a peripheral portion of a rotation-symmetry-type lens. Spherical aberration is a phenomenon where a light which passes through the center portion of the lens and a light which passes through the peripheral portion of the lens do not converge on the same focal point.

Figure 1:
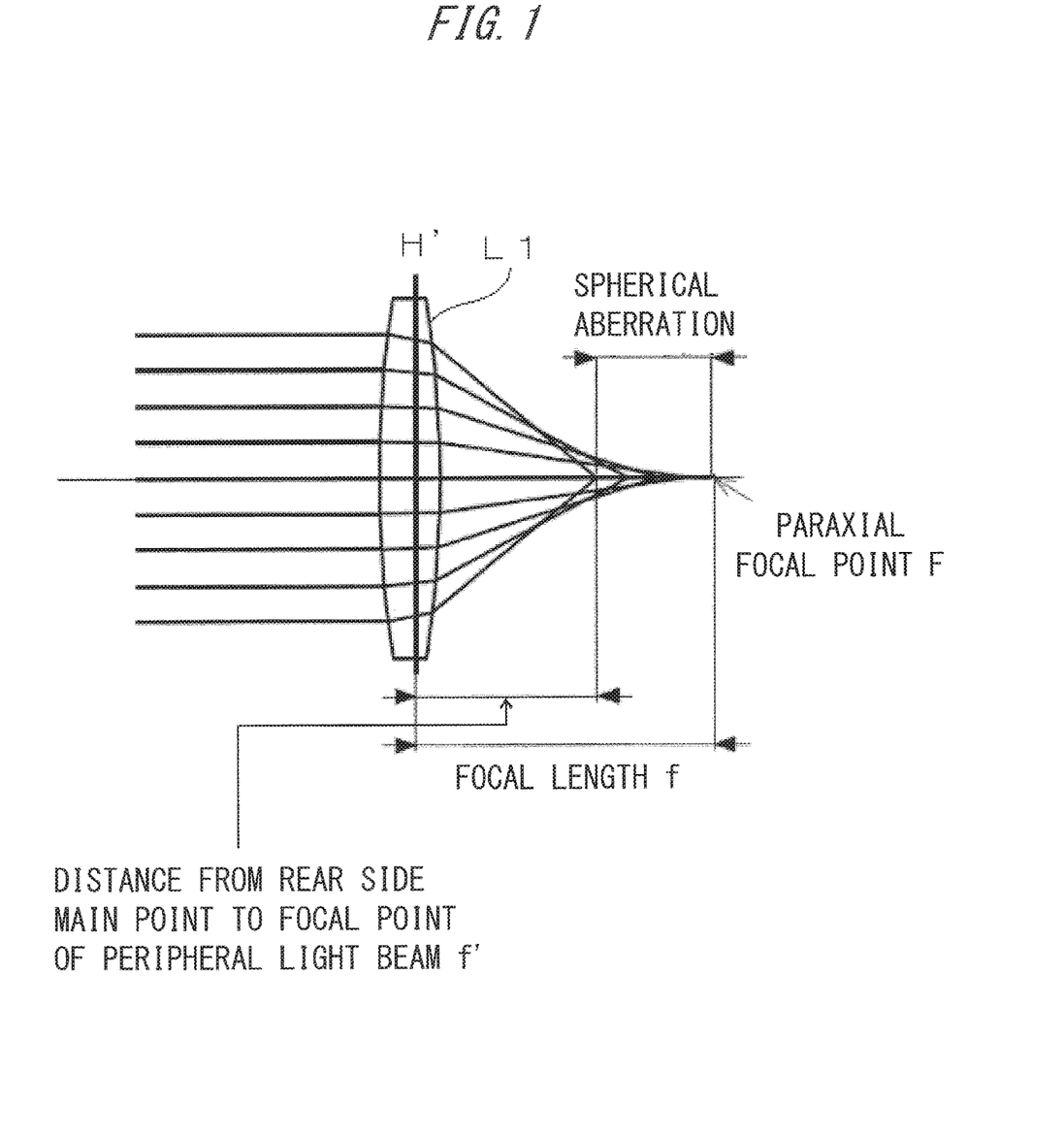
FIG. 1 is a schematic diagram illustrating spherical aberration of a lens.

As illustrated in FIG. 1, assuming a rear principal point of a lens L1 as H', a paraxial focal point as F, a focal length as f, and a distance from the rear principal point H' to a focal point of a peripheral light beam (a light which passes through a peripheral portion of the lens) as f', paraxial refractivity of the lens L1 P is expressed by the following formula (1) using the focal length f. Although the description is made with respect to the case where air is present in front of and behind the lens and a refractive index is set to 1, the present invention is not limited to such a case.

$$P = \frac{1}{f} \tag{1}$$

In this embodiment, the case where spherical aberration is generated means the case where the position of a focal point F' of a peripheral light beam and the position of the paraxial focal point F differ from each other, and refractivity P' of a peripheral portion of the lens L1 is expressed by the following formula (2) using the distance f'.

$$P' = \frac{1}{f'} \tag{2}$$

In FIG. 1, the focal point F' of the peripheral light beam is closer to the rear principal point H' than the paraxial focal point F is and hence, the following formula (3) is established. That is, when spherical aberration is generated in the lens L1, difference is generated in refractivity between the center portion and the peripheral portion of the lens L1.

$$P < P' \tag{3}$$

Figure 2A:
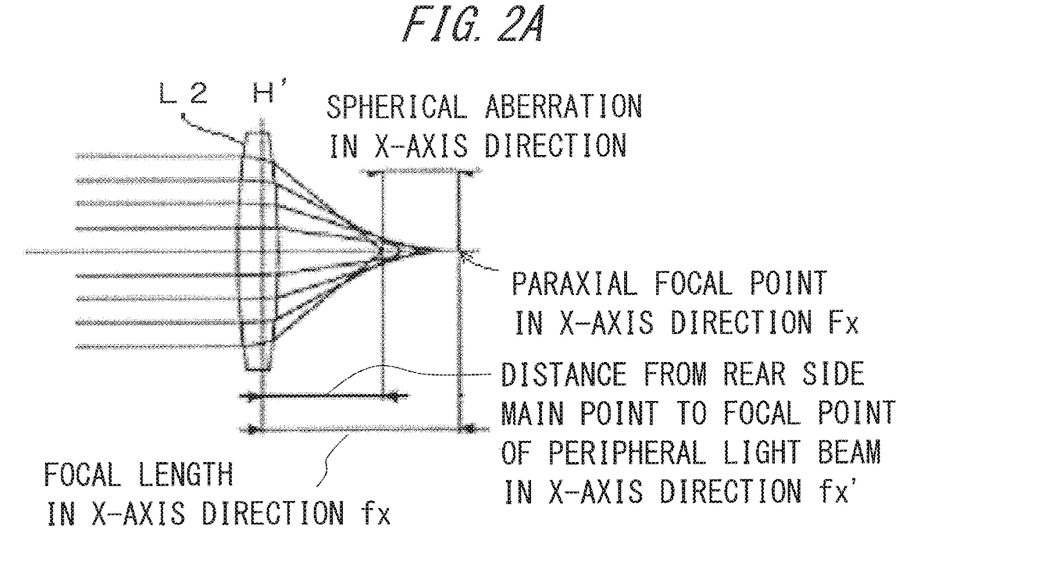
FIG. 2A and FIG. 2B are schematic diagrams illustrating spherical aberration of a toric lens.
Figure 2B:
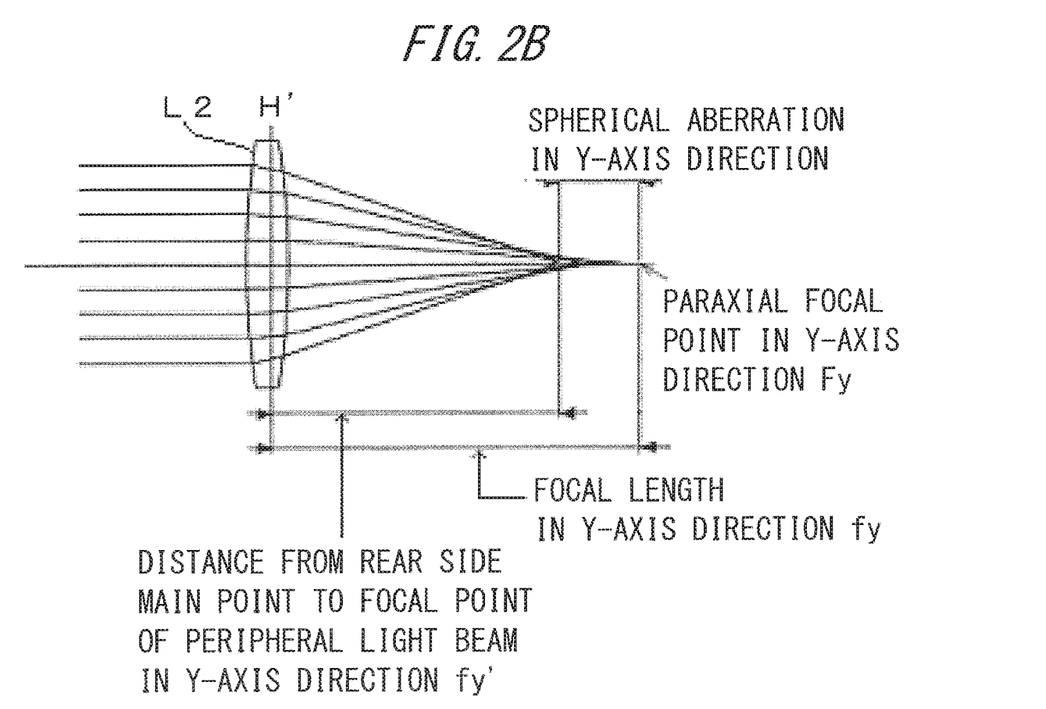

Next, spherical aberration generated in a toric lens L2 is described with reference to FIG. 2A and FIG. 2B. For the sake of convenience of description, the description is made by assuming that an optical axis of the toric lens L2 is taken on a Z axis, an XY plane orthogonal to the optical axis is set and an X axis and a Y axis are orthogonal to each other. However, the X axis and the Y axis may not be always orthogonal to each other, and may be configured such that the X axis extends in a first direction on the XY plane and the Y axis extends in a second direction which differs from the first direction. FIG. 2A and FIG. 2B illustrate states where light beams in the X axis direction and Y axis direction of the toric lens L2 converge respectively. As illustrated in FIG. 2A, it is assumed that a rear principal point of the toric lens L2 is H', a paraxial focal point in the X axis direction of the lens is Fx, a focal length in the X axis direction of the lens is fx, and a distance from a rear principal point H' to a focal point of a peripheral light beam in the X axis direction of the lens is fx'. In the same manner, as illustrated in FIG. 2B, Fy, fy, fy' are respectively set also with respect to the Y axis direction of the lens.

In this case, as described with reference to FIG. 1, the following formulas (4) to (7) are established.

$$P_x = \frac{1}{f_x} \tag{4}$$

$$P'_x = \frac{1}{f'_x} = \frac{1}{f_x + SA_x} \tag{5}$$

$$P_y = \frac{1}{f_y} \tag{6}$$

$$P'_y = \frac{1}{f'_y} = \frac{1}{f_y + SA_y} \tag{7}$$

Here, SAx, SAy indicate a distance of amounts of spherical aberration in the X axis direction of the lens and a distance of amounts of spherical aberration in the Y axis direction of the lens respectively. For example, SAx, SAy in the toric lens L2 illustrated in FIG. 2A and FIG. 2B take negative values.

Cylindrical refractivity Pc in a paraxial portion of the toric lens L2 and cylindrical refractivity Pc' in a peripheral portion of the toric lens L2 are expressed by the following formulas (8) and (9). Both cylindrical refractivities Pc, Pc' correspond to the difference between refractivity in the first direction and refractivity in the second direction. Further, Px, Px', Py and Py' respectively correspond to the first refractivity, second refractivity, third refractivity and fourth refractivity.

$$P_C = P_x - P_y \tag{8}$$

$$P_C' = P_x' - P_y' \tag{9}$$

In this embodiment, for the purpose of alleviating astigmatism of a cornea in the radial direction or in the circumferential direction by measuring a shape of an eyeball, a toric intraocular lens is manufactured by determining Pc and Pc' on a lens side such that cylindrical refractivities of a paraxial portion and a peripheral portion of an eye into which the intraocular lens is inserted cancel each other in the formulas (8) and (9). Alternatively, a toric intraocular lens is manufactured by individually determining SAx, SAy such that cylindrical refractivities of a paraxial portion and a peripheral portion of an eye into which the intraocular lens is inserted cancel each other in the formulas (5) and (7). Accordingly, not only amounts of astigmatism in the center portion of the lens but also amounts of astigmatism in the peripheral portion of the lens can be controlled, and hence, it is possible to provide a lens having a more favorable astigmatism correcting function compared to a conventional toric intraocular lens. The toric intraocular lens according to the present invention is not limited to the configuration where the difference in refractivity differs in two stages between a paraxial portion and a peripheral portion, and the toric intraocular lens may be configured such that the difference in refractivity continuously varies in a stepless manner from the center to the periphery of the lens.

Figure 3:
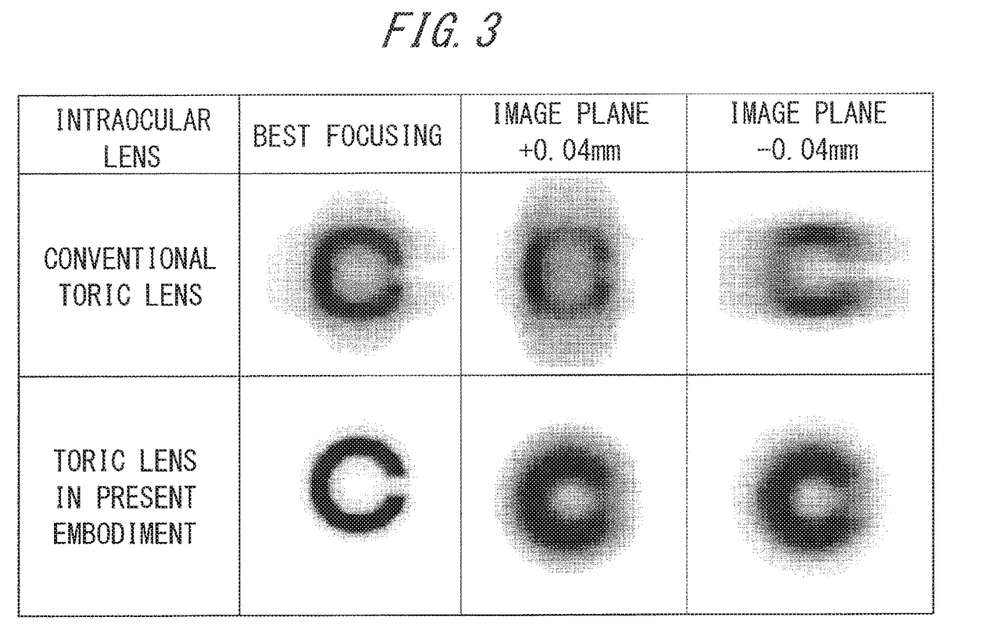
FIG. 3 is a table illustrating one example of a simulation result of a toric intraocular lens according to this embodiment and a conventional toric intraocular lens.

Next, in this embodiment, with reference to FIG. 3, the description is made with respect to a simulation result on Landolt ring images acquired by a toric intraocular lens when the toric intraocular lens is designed using the formulas (8) and (9). FIG. 3 illustrates Landolt ring images in so-called best focusing where a conventional toric lens and a toric lens according to this embodiment are applied to an astigmatic eye under a predetermined condition as intraocular lenses, Landolt ring images acquired when an image plane is moved away from the lens by 0.04 mm (+) in the simulation, and Landolt ring images when the image plane is made to approach the lens by 0.04 mm (−).

As can be understood from the Landolt rings in best focusing illustrated in FIG. 3, in the toric intraocular lens according to this embodiment, astigmatism is favorably reduced so that a clear Landolt ring image is acquired. On the other hand, in the conventional toric intraocular lens, although a Landolt ring image is confirmed to an extent that the image is recognizable, so-called blurring is generated around the Landolt ring.

Further, the difference in Landolt ring image appears also when an image plane is moved so that the image is defocused. As illustrated in FIG. 3, in the toric intraocular lens according to this embodiment, even when an image plane is displaced from the position for best focusing, blurring having a rotation symmetrical shape is generated. That is, it is safe to say that astigmatism is substantially completely eliminated. On the other hand, in the conventional toric intraocular lens, blurring extends in a longitudinal direction (vertical direction on a paper on which FIG. 3 is drawn) (image plane: +0.04 mm) or extends in a lateral direction (left-and-right direction on the paper on which FIG. 3 is drawn) (image plane: −0.04 mm) and, hence, it is understood that astigmatism is not completely eliminated. From the above, it is safe to say that the toric intraocular lens according to this embodiment can acquire more effective astigmatism correction effect compared to the prior art.

Figure 4:
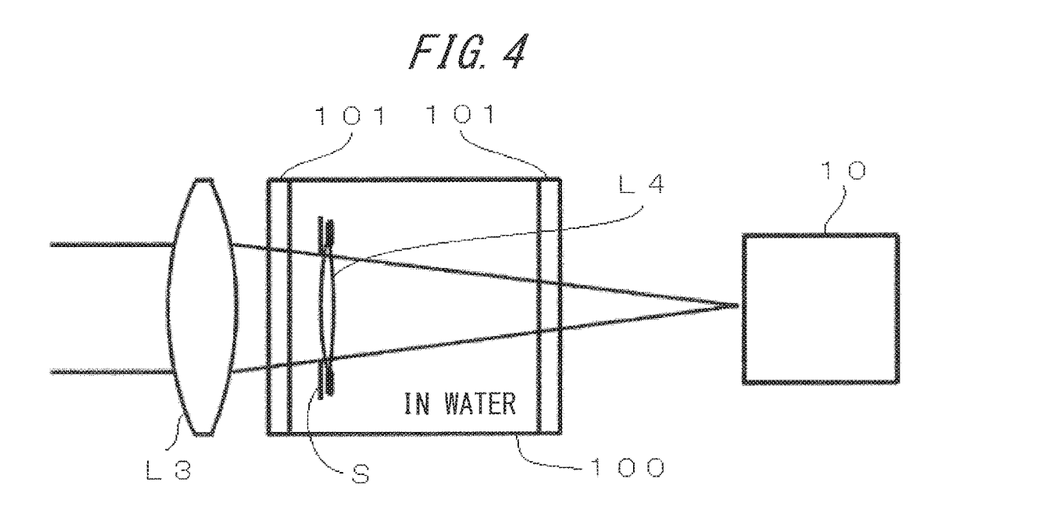
FIG. 4 is a diagram illustrating the schematic constitution of a schematic eye prepared for evaluating the toric intraocular lens.

Next, the description is made on an evaluation result with respect to the case where an astigmatism cornea lens which differs in amounts of astigmatism between a center portion and a peripheral portion of the lens is manufactured. FIG. 4 illustrates the schematic configuration of a schematic eye used for the evaluation. In the schematic eye illustrated in FIG. 4, an astigmatism cornea lens L3 is suitably rotatable about an optical axis. Accordingly, it is possible to make an astigmatism axis of the astigmatism cornea lens L3 and an astigmatism axis of a toric intraocular lens L4 agree with each other. In FIG. 4, the astigmatism cornea lens L3 is formed of a biconvex lens. However, the astigmatism cornea lens L3 may be a meniscus lens or a biconcave lens.

In the schematic eye illustrated in FIG. 4, the toric intraocular lens L4 is arranged in water by estimating the case where the toric intraocular lens L4 is disposed inside the eye. However, the schematic eye may be configured such that the toric intraocular lens L4 is arranged in air. As indices to be observed with respect to the schematic eye illustrated in FIG. 4, Landolt rings described on a visual acuity chart having a length of 3 m are used. An index to be imaged is an optotype of 1.0 vision. A filter which allows light of 546 nm to pass therethrough is mounted on a halogen lump which forms a light source, and light which passes through the filter is irradiated to the visual acuity chart from a back side of the visual acuity chart. A camera 10 can move back-and-forth in a direction with respect to an optical axis of the toric intraocular lens L4 for focusing. As illustrated in FIG. 4, the toric intraocular lens L4 is positioned inside an approximately rectangular parallelepiped casing 100 where both surfaces of the casing 100 are formed of planar glasses 101, 101. As described previously, the inside of the casing 100 is filled with water, and a stop S is mounted on an astigmatism cornea lens L3 side of the toric intraocular lens L4.

Figure 5:
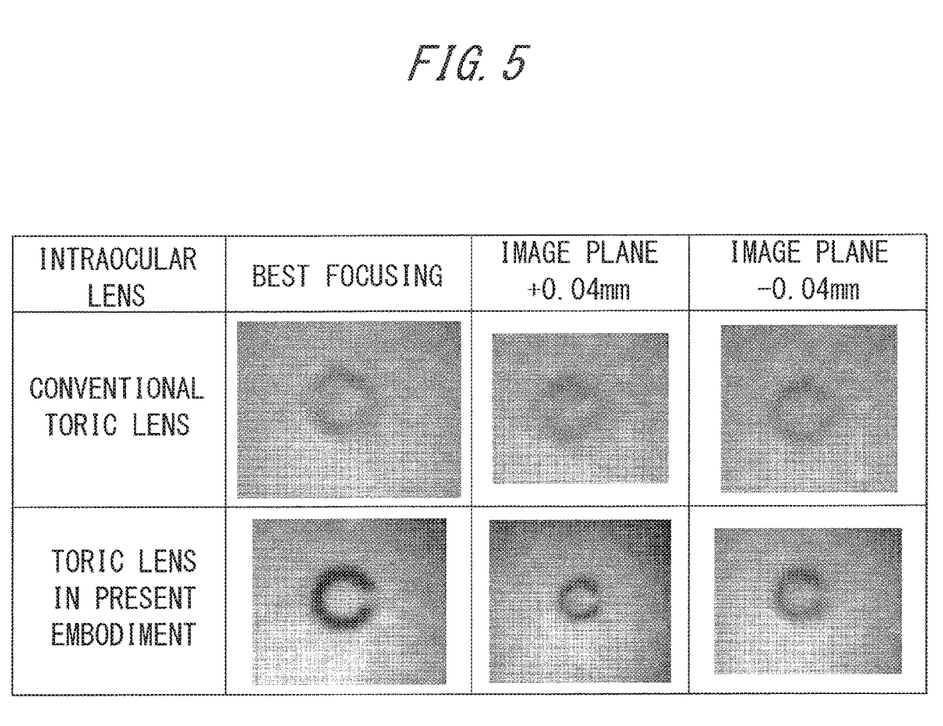
FIG. 5 is a table illustrating one example of the evaluation result of the schematic eye illustrated in FIG. 4.

FIG. 5 illustrates a result obtained by imaging Landolt rings which are indexes by a camera when the schematic eye illustrated in FIG. 4 is used. As illustrated in FIG. 5, in the same manner as the simulation result illustrated in FIG. 3, in the toric intraocular lens L4 of this embodiment, Landolt rings are clearly imaged in best focusing. Further, also with respect to images which are intentionally defocused by moving the camera 10 in an optical axis direction of the toric intraocular lens L4, blurring occurs in rotation symmetry. Accordingly, it is understood that astigmatism is favorably reduced. On the other hand, in the conventional toric intraocular lens, although Landolt rings are recognized in best focusing, images are remarkably degraded when the images are intentionally defocused. Accordingly, it is understood that astigmatism is not sufficiently reduced.

Figure 6A:
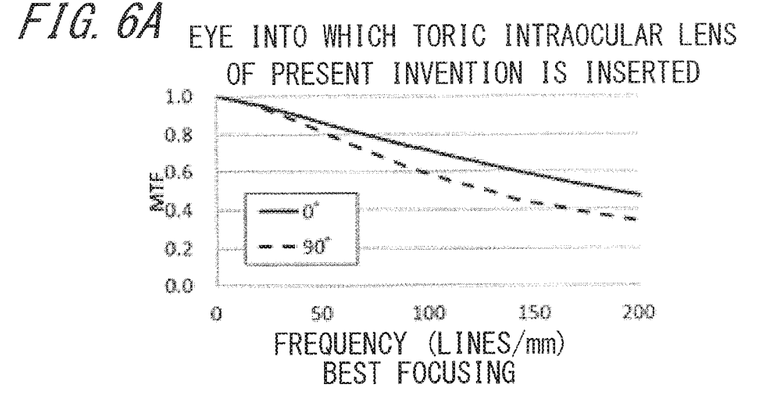
FIGS. 6A to 6C are graphs illustrating one example of a measurement result of an MTF of the toric intraocular lens according to this embodiment.
Figure 6B:
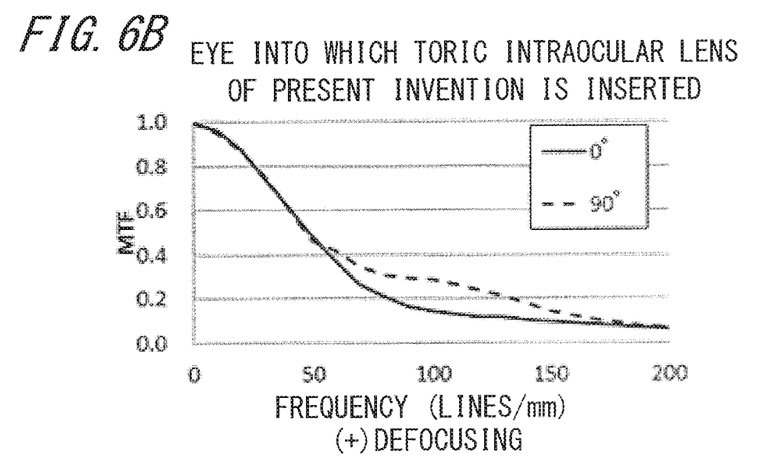
Figure 6C:
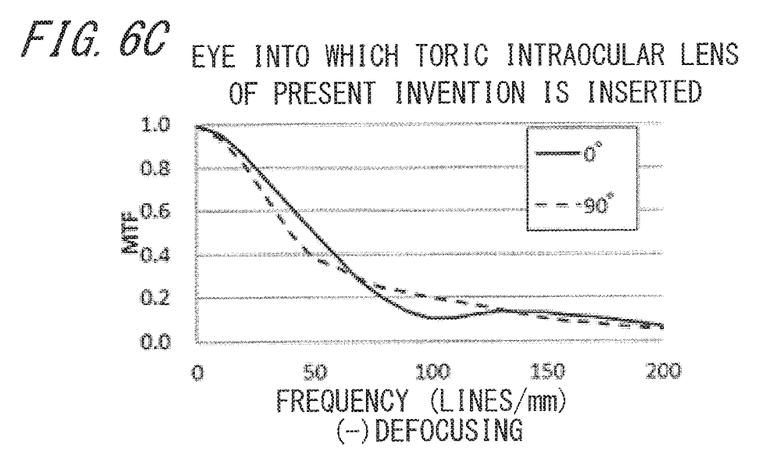

FIGS. 6A to 6C illustrate a result obtained by measuring MTF (Modulation Transfer Function) of the toric intraocular lens of this embodiment using the configuration of the schematic eye illustrated in FIG. 5. In the drawings, spatial frequency indicative of a distance of stripes of a stripe pattern used as an object to be imaged is taken on an axis of abscissas, and a value of MTF of an image of the stripe pattern focused on a light receiving surface of a camera by the toric intraocular lens is illustrated on an axis of ordinates. A solid line indicates numerical values in a sagittal (radiation) direction of the toric intraocular lens (0 degree direction in this case), and a broken line indicates numerical values in a meridional (concentric) direction of the toric intraocular lens (90 degree direction in this case). As illustrated in FIGS. 6A to 6C, in the case of the schematic eye into which the toric intraocular lens of this embodiment is inserted, it is understood that MTF exhibits favorable values both in the 0 degree direction and in the 90 degree direction in best focusing. Further, even in defocusing, although values of MTF are lowered, MTF exhibits substantially the same change both in the 0 degree direction and in the 90 degree direction, and hence, it is understood that astigmatism is substantially not generated.

Figure 7A:
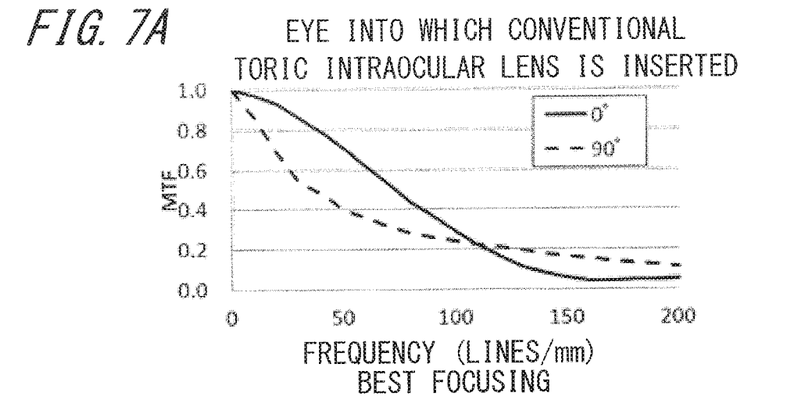
FIGS. 7A to 7C are graphs illustrating one example of a measurement result of an MTF of a conventional toric intraocular lens.
Figure 7B:
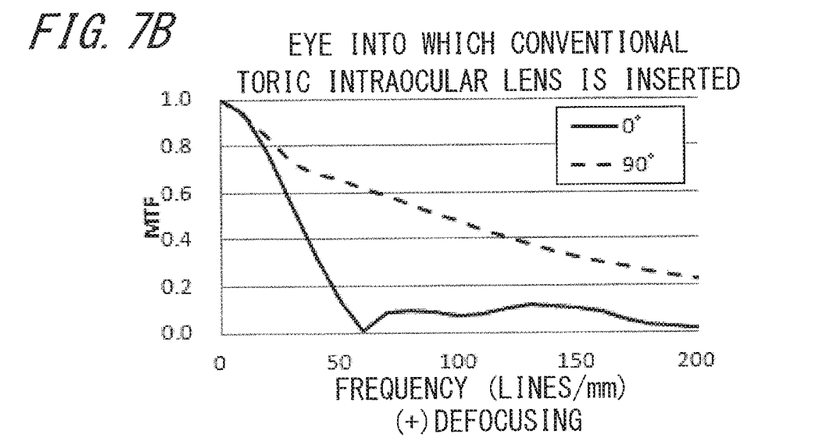
Figure 7C:
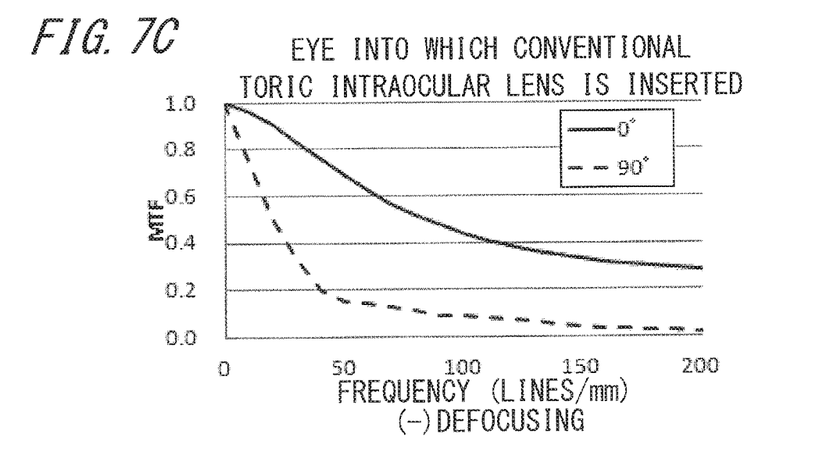

Next, FIGS. 7A to 7C illustrate a result obtained by measuring MTF of a conventional toric intraocular lens using the configuration of the schematic eye illustrated in FIG. 5. As illustrated in FIGS. 7A to 7C, in the conventional toric intraocular lens, MTF at spatial frequency of 100 lines/mm is 0.2 or more in best focusing, and hence, it is considered that the schematic eye can see the vision of 1.0. However, as can be understood from FIGS. 6A to 6C, MTF exhibits low values compared to the toric intraocular lens of this embodiment. Further, as illustrated in FIGS. 7A to 7C, in the conventional toric intraocular lens, MTF exhibits different changes in the 0 degree direction and in the 90 degree direction even at the time of defocusing. Accordingly, it is safe to say that astigmatism still remains in the conventional toric intraocular lens. As has been set forth above, with the use of the toric intraocular lens which is designed in the above-mentioned manner by taking into account not only amounts of astigmatism at a center portion of the lens but also amounts of astigmatism at a peripheral portion of the lens in accordance with this embodiment, the correction of astigmatism can be performed more favorably compared to the prior art.

REFERENCE SIGNS LIST

L1 lens
L2 toric lens
L3 astigmatism cornea lens
L4 toric intraocular lens

What is claimed is:

1. A toric ophthalmic lens wherein refractivity of the lens differs between a first radial direction of the lens on a plane perpendicular to an optical axis of the lens and a second radial direction of the lens which differs from the first radial direction,
wherein refractivity difference which is the difference between the refractivity at a first position that resides on a line extending in the first radial direction and the refractivity at a second position that resides on a line extending in the second radial direction and corresponds to the first position continuously varies in a stepless manner according to a variation of the first position and the second position from the center of the lens.

2. The toric ophthalmic lens according to claim 1, wherein the refractivity difference is controlled based on a measurement of a shape of cornea of an eyeball in which the lens is mounted or a measurement of a distribution of refractive power from a center to a periphery of the cornea to vary so as to attenuate a variation in refractivity with respect to a radial direction or a circumferential direction in a cornea of the eyeball.

3. The toric ophthalmic lens according to claim 2, wherein with respect to first refractivity in a paraxial portion of the lens in the first radial direction, second refractivity in a peripheral portion of the lens in the first radial direction, third refractivity in the paraxial portion of the lens in the second radial direction, and fourth refractivity in the peripheral portion of the lens in the second radial direction, the difference between the first refractivity and the third refractivity is refractivity difference in the paraxial portion of the lens and the difference between the second refractivity and the fourth refractivity is refractivity difference in the peripheral portion of the lens, and the refractivity difference in the paraxial portion of the lens and the refractivity difference in the peripheral portion of the lens are controlled to be different from each other.

4. The toric ophthalmic lens according to claim 3, wherein amounts of first spherical aberration in the first radial direction and amounts of second spherical aberration in the second radial direction are controlled individually.

5. The toric ophthalmic lens according to claim 2, wherein amounts of first spherical aberration in the first radial direction and amounts of second spherical aberration in the second radial direction are controlled individually.

6. The toric ophthalmic lens according to claim 1, wherein with respect to first refractivity in a paraxial portion of the lens in the first radial direction, second refractivity in a peripheral portion of the lens in the first radial direction, third refractivity in the paraxial portion of the lens in the second radial direction, and fourth refractivity in the peripheral portion of the lens in the second radial direction, the difference between the first refractivity and the third refractivity is refractivity difference in the paraxial portion of the lens and the difference between the second refractivity and the fourth refractivity is refractivity difference in the peripheral portion of the lens, and the refractivity difference in the paraxial portion of the lens and the refractivity difference in the peripheral portion of the lens are controlled to be different from each other.

7. The toric ophthalmic lens according to claim 6, wherein amounts of first spherical aberration in the first radial direction and amounts of second spherical aberration in the second radial direction are controlled individually.

8. The toric ophthalmic lens according to claim 1, wherein amounts of first spherical aberration in the first radial direction and amounts of second spherical aberration in the second radial direction are controlled individually.

9. A toric ophthalmic lens wherein refractivity of the lens differs between a first radial direction of the lens on a plane perpendicular to an optical axis of the lens and a second radial direction of the lens which differs from the first radial direction, wherein the following formulas (1) to (6) are established, $$P_1 = \frac{1}{f_1} \quad (1)$$

$$P_1' = \frac{1}{f_1'} = \frac{1}{f_1 + SA_1} \quad (2)$$

$$P_2 = \frac{1}{f_2} \quad (3)$$

$$P_2' = \frac{1}{f_2'} = \frac{1}{f_2 + SA_2} \quad (4)$$

$$P_C = P_1 - P_2 \quad (5)$$

$$P_C' = P_1' - P_2' \quad (6)$$

wherein $P_1$ is first refractivity at a first position in a paraxial portion of the lens that resides on a first line extending in the first radial direction, $P_1'$ is second refractivity at a second position in a peripheral portion of the lens that resides on the first line extending in the first radial direction, $P_2$ is third refractivity at a third position corresponding to the first position in the paraxial portion of the lens that resides on a second line extending in the second radial direction, $P_2'$ is fourth refractivity at a fourth position corresponding to the second position in the peripheral portion of the lens that resides on the second line extending in the second radial direction, $f_1$ is a focal length in the first radial direction of the lens, $SA_1$ is a distance of amounts of spherical aberration at the second position in the first radial direction of the lens, $f_2$ is a focal length in the second radial direction of the lens, $SA_2$ is a distance of amounts of spherical aberration at the fourth position in the second radial direction of the lens, $P_C$ and $P_C'$ are determined based on a measurement of an eyeball in which the lens is mounted so as to cancel a difference between a refractivity in the paraxial portion of the eyeball and a refractivity in the peripheral portion of the eyeball, respectively, and $P_C$ and $P_C'$ are configured to continuously vary in a stepless manner.

* * * * *